(12) United States Patent
Lange et al.

(10) Patent No.: US 10,307,187 B2
(45) Date of Patent: Jun. 4, 2019

(54) SPINAL IMPLANT SYSTEM AND METHOD

(71) Applicant: WARSAW ORTHOPEDIC, INC., Warsaw, IN (US)

(72) Inventors: Eric C. Lange, Collierville, TN (US); Darren L. Davis, Arlington, TN (US)

(73) Assignee: Warsaw Othopedic, Inc., Warsaw, IN (US)

( * ) Notice: Subject to any disclaimer, the term of this patent is extended or adjusted under 35 U.S.C. 154(b) by 0 days.

(21) Appl. No.: 15/561,280

(22) PCT Filed: Mar. 22, 2016

(86) PCT No.: PCT/US2016/023550
§ 371 (c)(1),
(2) Date: Sep. 25, 2017

(87) PCT Pub. No.: WO2016/154185
PCT Pub. Date: Sep. 29, 2016

(65) Prior Publication Data
US 2018/0116697 A1     May 3, 2018

Related U.S. Application Data

(63) Continuation of application No. 14/669,696, filed on Mar. 26, 2015, now abandoned.

(51) Int. Cl.
*A61B 17/70* (2006.01)

(52) U.S. Cl.
CPC ...... *A61B 17/7067* (2013.01); *A61B 17/7068* (2013.01)

(58) Field of Classification Search
CPC ............ A61B 17/7062; A61B 17/7065; A61B 17/7067; A61B 17/7068; A61B 17/707; A61B 17/7071; A61B 17/7073; A61B 17/82; A61B 17/842; A61B 17/80–17/8095; A61F 2/4405

See application file for complete search history.

(56) References Cited

U.S. PATENT DOCUMENTS

| | | | |
|---|---|---|---|
| 8,409,287 B2* | 4/2013 | Braddock, Jr. | A61F 2/4425 623/17.15 |
| 8,636,774 B2 | 1/2014 | Abrahams et al. | |
| 9,119,680 B2* | 9/2015 | Altarac | A61B 17/7065 |
| 2003/0028250 A1* | 2/2003 | Reiley | A61F 2/4405 623/17.11 |
| 2009/0062915 A1* | 3/2009 | Kohm | A61B 17/7038 606/280 |
| 2013/0012996 A1* | 1/2013 | Zamani | A61B 17/7068 606/248 |
| 2013/0030471 A1 | 1/2013 | Ramsay et al. | |
| 2013/0296939 A1 | 11/2013 | Perkins | |
| 2013/0304125 A1 | 11/2013 | Timm et al. | |

OTHER PUBLICATIONS

International Search Report and Written Opinion of the International Searching Authority—ISA-Korean Intellectual Property Office, 189 Cheongsa-ro, Seo-gu, Daejeon, Republic of Korea PCT/US16/23550 dated Jun. 1, 2016.

* cited by examiner

*Primary Examiner* — Lynnsy Summitt

(57) ABSTRACT

An interspinous implant comprises a first member and a second member. The members define a pathway. A third member is movable along the pathway relative to the first member and the second member. Systems and methods are disclosed.

20 Claims, 14 Drawing Sheets

SPINAL IMPLANT SYSTEM AND METHOD

TECHNICAL FIELD

The present disclosure generally relates to medical devices for the treatment of musculoskeletal disorders, and more particularly to a surgical system that includes a spinal implant and method for treating a spine.

BACKGROUND

Spinal disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including pain, nerve damage, and partial or complete loss of mobility. For example, after a disc collapse, severe pain and discomfort can occur due to the pressure exerted on nerves and the spinal column.

Non-surgical treatments, such as medication, rehabilitation and exercise can be effective, however, may fail to relieve the symptoms associated with these disorders. Surgical treatment of these spinal disorders includes decompression, discectomy, laminectomy, laminoplasty, fusion, fixation and implantable prosthetics. For example, spinal stabilization treatments may employ implants, which may include interbody devices, plates and bone fasteners to stabilize vertebrae and facilitate healing. This disclosure describes an improvement over these technologies.

SUMMARY

In one embodiment, an interspinous implant is provided. The interspinous implant comprises a first member and a second member. The members define a pathway. A third member is movable along the pathway relative to the first member and the second member. In some embodiments, systems and methods are provided.

BRIEF DESCRIPTION OF THE DRAWINGS

The present disclosure will become more readily apparent from the specific description accompanied by the following drawings, in which.

DETAILED DESCRIPTION

Figure 1:
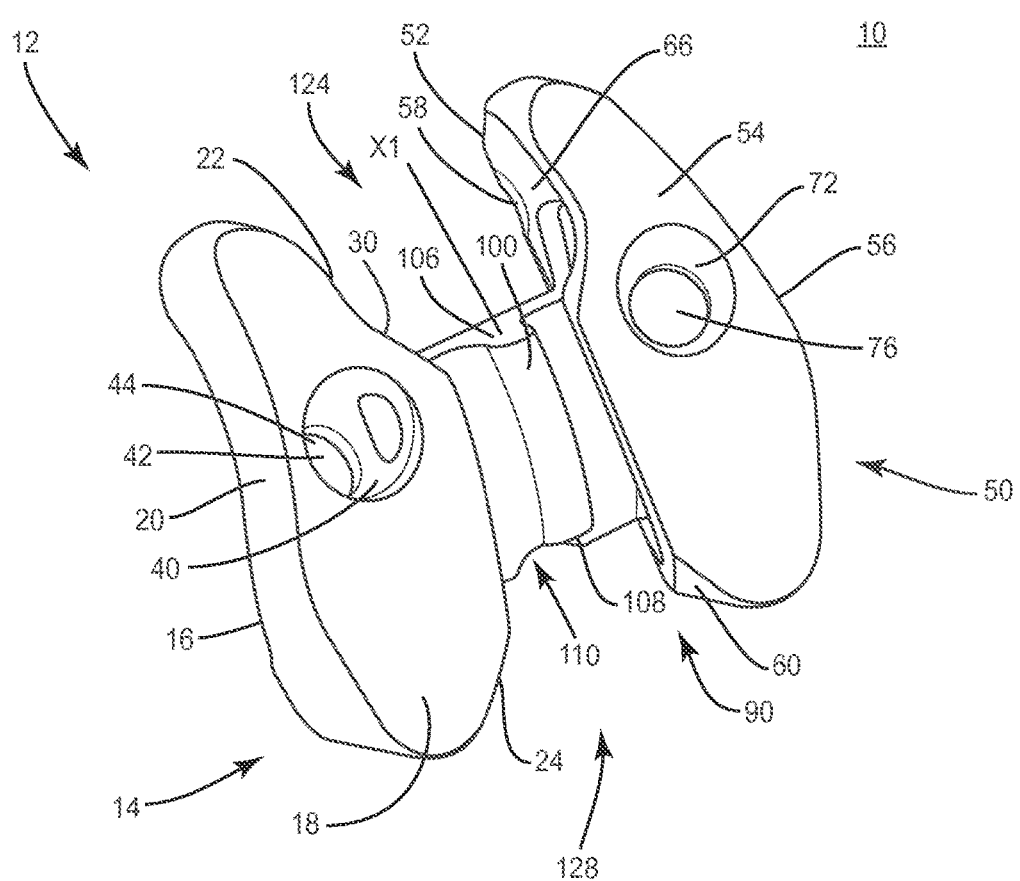
FIG. 1 is a perspective view of components of one embodiment of a surgical system in accordance with the principles of the present disclosure.
Figure 2:
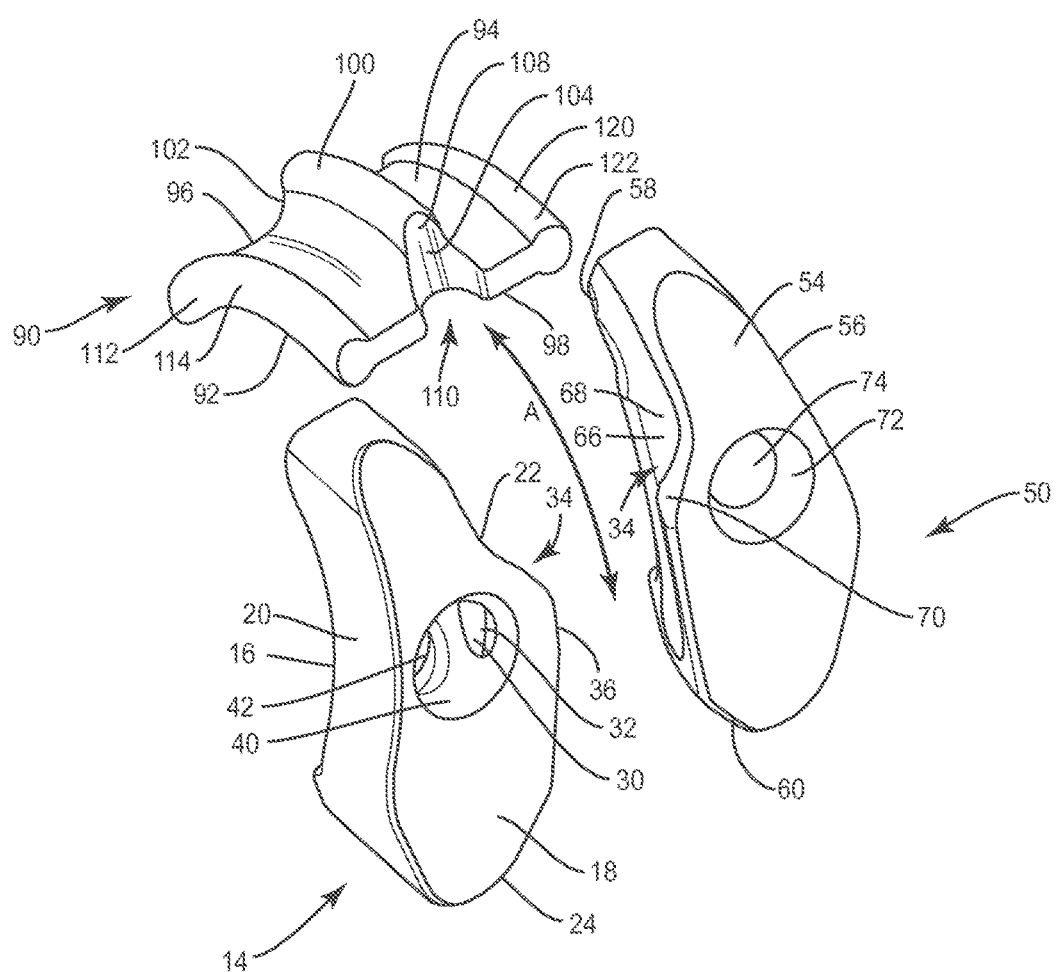
FIG. 2 is a perspective view of the components shown in FIG. 1 with parts separated.

The exemplary embodiments of the surgical system and related methods of use disclosed are discussed in terms of medical devices for the treatment of musculoskeletal disorders and more particularly, in terms of a surgical system including a spinal implant and a method for treating a spine. In some embodiments, the systems and methods of the present disclosure are employed with a spinal joint fusion, for example, with a cervical, thoracic, lumbar and/or sacral region of a spine. In some embodiments, the spinal implant includes an interbody device, interspinous implant and/or bone fasteners. In some embodiments, the systems and methods of the present disclosure are employed with decompression, discectomy, laminectomy, laminoplasty, fusion, fixation and implantable prosthetic procedures.

In some embodiments, the surgical system includes a spinal implant comprising a facet fixation interspinous process implant. In some embodiments, the surgical system includes a spinal implant comprising a fixation implant having a curved surface to conform to the spinous process and provide a stable implant. In some embodiments, the spinal implant includes openings for disposal of screws. In some embodiments, the screws are placed through the facet joints at angles that are stable and offer less risk to adjacent neural structures.

In some embodiments, the surgical system includes a spinal implant comprising an interspinous spacer having outer portions and an intermediate portion. In some embodiments, the surgical system includes a spinal implant comprising an interspinous spacer having outer portions and an intermediate, movable portion. In some embodiments, the intermediate portion is a central movable portion that is translatable relative to the outer portions. In some embodiments, the outer portions include screw holes. In some embodiments, the outer portions comprise wings that include screw holes. In some embodiments, the central portion of the implant is configured for translation in a cranial-caudal direction relative to the outer portions to conform to the patient anatomy at one or more vertebral levels. In some embodiments, one or more of the outer portions include a bump stop to resist and/or prevent the intermediate portion from sliding entirely out of the track of the outer portions. In some embodiments, a medial surface of each of the outer portions includes a groove disposed for clearance with an inferior lamina. In some embodiments, the intermediate portion mates with an inferior spinous process more posterior than the superior spinous process such that an inferior surface of the spacer does not project inside the spinal canal. In some embodiments, one or more of the outer portions include a mating element that matingly engages a mating element of the intermediate portion to resist and/or prevent non-desirable assembly orientation of the portions of the spinal implant.

In some embodiments, the surgical system includes a spinal implant comprising an anatomical curve and a bottom surface that is contoured to match and/or mate with anatomy. In some embodiments, the surgical system includes a spinal implant having a plate comprising an anatomical contour surface that engages flush with a patient anatomy to provide stability and an effective screw trajectory.

In some embodiments, the surgical system includes a spinal implant comprising a lamina notch. In some embodiments, the lamina notch facilitates engagement of the spinal implant with a spinous process/laminar intersection. In some embodiments, the spinal implant includes an inferior portion and/or a foot configured to provide stability when disposed with an inferior lamina. In some embodiments, the spinal implant comprises a superior notch of one or more of the member. In some embodiments, the spinal implant comprises a notch on a superior surface of the intermediate portion and an inferior notch that provide for stabilization and centering of the spinal implant with spinous processes.

In some embodiments, the surgical system includes a spinal implant comprising openings, such as, for example, screw holes. In some embodiments, the screw holes are disposed at an angular orientation. In some embodiments, the angular orientation is 40 degrees. In some embodiments, the screw holes comprise insertion holes. In some embodiments, the spinal implant includes a facet screw plate having a mating curvature. In some embodiments, the spinal implant includes a screw trajectory oriented through a facet and a pedicle. In some embodiments, the spinal implant comprises a trans-facet joint screw assembly, which includes at least one trans-facet screw trajectory. In some embodiments, the outer portions include one or more central holes for attachment with an implant inserter.

In some embodiments, the surgical system includes a spinal implant comprising a modular plate. In some embodiments, the plate includes a middle interspinous portion. In some embodiments, the interspinous portion is modular. In some embodiments, the plate is adjustable to conform to a patient anatomy. In some embodiments, the spinal implant includes a plurality of interspinous portions having alternate heights and widths to conform and/or adjust to a patient anatomy. In some embodiments, the interspinous portion is movable relative to the screw holes to accommodate a patient anatomy at different spinal levels. In some embodiments, the interspinous portion optimizes an implant plate height and width and the screw trajectory for each spinal level.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. Also, in some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, micro discectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, muscle, ligaments, tendons, cartilage and/or bone unless specifically referred to otherwise.

The following discussion includes a description of a surgical system and related methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1-5, there are illustrated components of a surgical system, such as, for example, a spinal implant system 10.

The components of spinal implant system 10 can be fabricated from biologically acceptable materials suitable for medical applications, including metals, synthetic polymers, ceramics and bone material and/or their composites. For example, the components of spinal implant system 10, individually or collectively, can be fabricated from materials such as stainless steel alloys, commercially pure titanium, titanium alloys, Grade 5 titanium, super-elastic titanium alloys, cobalt-chrome alloys, stainless steel alloys, super-elastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate such as hydroxyapatite (HA), corraline HA, biphasic calcium phosphate, tricalcium phosphate, or fluorapatite, tri-calcium phosphate (TOP), HA-TOP, calcium sulfate, or other resorbable polymers such as polyaetide, polyglycolide, polytyrosine carbonate, polycaroplaetohe and their combinations, biocompatible ceramics, mineralized collagen, bioactive glasses, porous metals, bone particles, bone fibers, morselized bone chips, bone morphogenetic proteins (BMP), such as BMP-2, BMP-4, BMP-7, rhBMP-2, or rhBMP-7, demineralized bone matrix (DBM), transforming growth factors (TGF, e.g., TGF-β), osteoblast cells, growth and differentiation factor (GDF), insulin-like growth factor 1, platelet-derived growth factor, fibroblast growth factor, or any combination thereof.

Various components of spinal implant system 10 may have material composites, including the above materials, to achieve various desired characteristics such as strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein. In one embodiment, a spinal implant, as described herein, may be formed substantially of a biocompatible metal, such as titanium and selectively coated with a bone-growth promoting material, such as HA. In one embodiment, a spinal implant, as described herein, may be formed substantially of a biocompatible polymer, such as PEEK, and selectively coated with a biocompatible metal, such as titanium, or a bone-growth promoting material, such as HA. In some embodiments, titanium may be plasma sprayed onto surfaces of the spinal implant to modify a radiographic signature of the spinal implant and/or improve bony ongrowth to the spinal implant by application of a porous or semi-porous coating of titanium.

Spinal implant system 10 may be employed, for example, with minimally invasive procedures, including percutaneous techniques, mini-open surgical techniques and/or open surgical techniques to deliver and introduce instrumentation and/or spinal implants, such as, for example, an interspinous implant at a surgical site within a body of a patient, which includes, for example, vertebrae. One or more of the components of surgical system 10 including an interspinous implant can be employed, for example, in decompression, discectomy, laminectomy, laminoplasty, fusion, fixation and implantable prosthetic procedures to treat patients suffering from a spinal disorder to provide stabilization and decompression. In some embodiments, one or more of the components of spinal implant system 10 is employed with a method for implanting an interspinous process spacer between two adjacent vertebrae, which includes introducing the interspinous spacer adjacent a superior and an inferior spinous processes.

Spinal implant system 10 includes an interspinous implant, such as, for example, a plate 12. In some embodiments, plate 12 is modular and comprises end members, as described herein, to facilitate selective adjustability with a patient anatomy. In some embodiments, one or more of the components and/or portions of plate 12 may have various cross-section configurations, such as, for example, flat, cylindrical, oval, oblong, triangular, rectangular, square, polygonal, irregular, uniform, non-uniform, variable and/or tapered. In some embodiments, one or more of the components and/or the overall geometry of plate 12 may have various configurations, such as, for example, oval, oblong, triangular, rectangular, square, polygonal, irregular, uniform, non-uniform, variable and/or tapered. Plate 12 defines a longitudinal axis X1.

Plate 12 includes an end member 14, which includes an anterior surface 16 and a posterior surface 18. Surface 16 is configured to engage tissue, such as, for example, vertebrae, as described herein. End member 14 includes an end surface 20. In some embodiments, surface 20 includes an undulating profile. In some embodiments, surface 20 may have alternate configurations, such as, for example, arcuate, irregular, uniform, non-uniform, variable and/or tapered. Surface 20 extends between surfaces 16, 18.

End member 14 includes a tissue engaging surface 22 engageable with vertebrae. In some embodiments, surface 22 includes an undulating profile. In some embodiments, all or a portion of surface 22 may have alternate configurations, such as, for example, arcuate, irregular, uniform, non-uniform, variable and/or tapered. Surface 22 extends between surfaces 16, 18. End member 14 includes a surface 24 configured for engagement with tissue, such as, for example, a spinous process. In some embodiments, surface 24 includes an angled profile. In some embodiments, surface 24 may have alternate configurations, such as, for example, arcuate, irregular, uniform, non-uniform, variable and/or tapered. Surface 24 extends between surface 16, 18. In some embodiments, surfaces 22, 24 may be rough, textured, porous, semi-porous, dimpled, knurled, toothed, grooved and/or polished to facilitate engagement with tissue.

End member 14 includes a surface 30 that defines a slot 32 having an arcuate configuration. Slot 32 defines a portion of a pathway, such as, for example, a track 34, as described herein. Slot 32 is configured for disposal of an intermediate member 90, as described herein, and surface 30 is engageable with intermediate member 90 in a keyed connection. Surface 30 includes a retention member, such as, for example, opposing flanges 36 disposed along slot 32 and configured to engage a portion of intermediate member 90 to retain intermediate member 90 with end member 14. As intermediate member 90 translates relative to end member 14, flanges 36 retain intermediate member 90 with end member 14.

Figure 8:
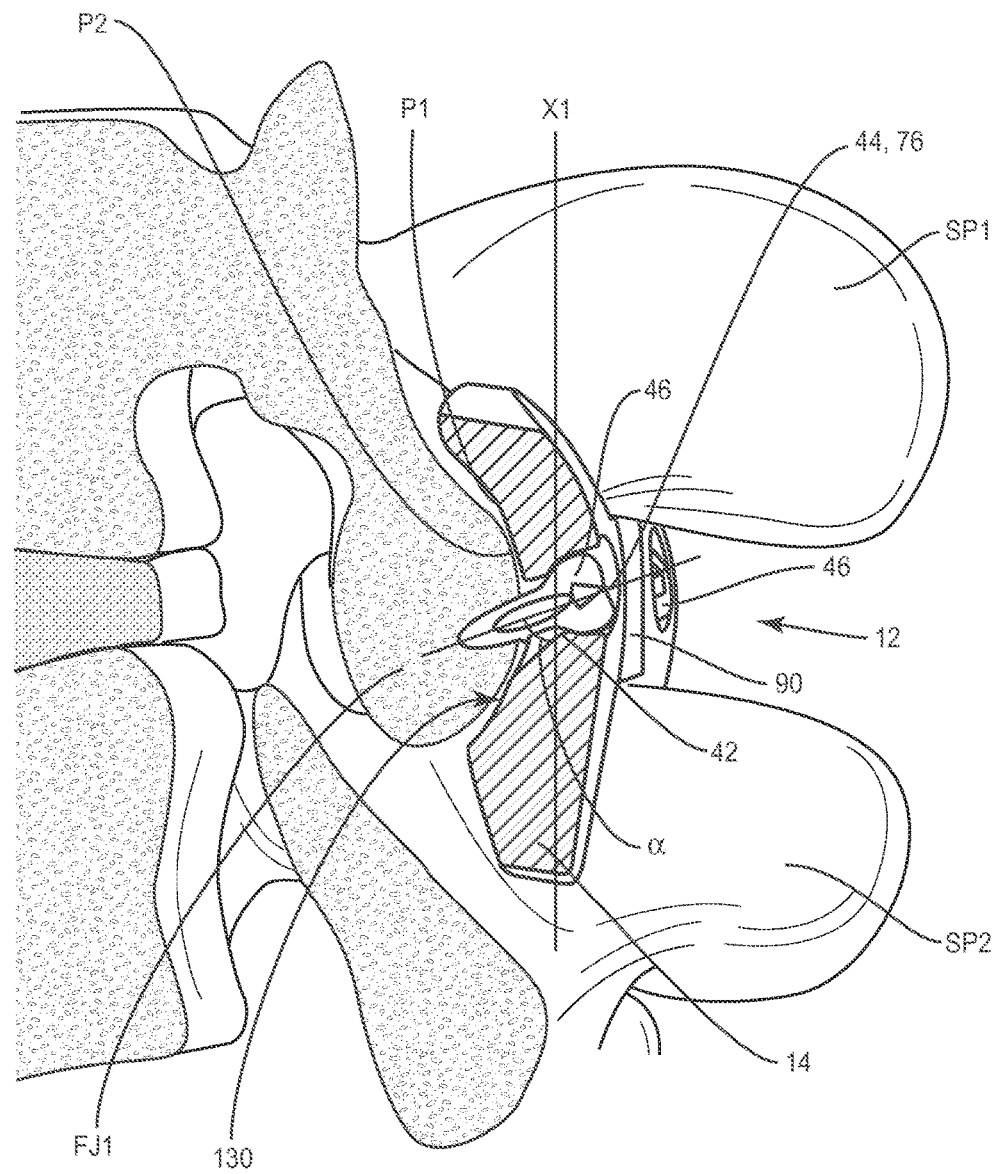
FIG. 8 is an enlarged view of the components and vertebrae shown in FIG. 7.
Figure 10:
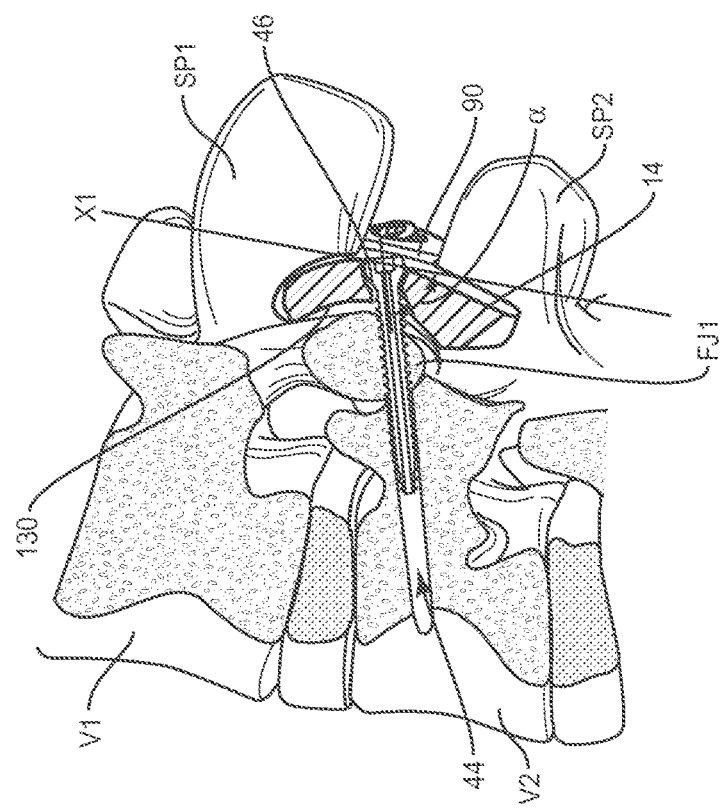
FIG. 10 is a side view of components of the components and vertebrae shown in FIG. 9.
Figure 9:
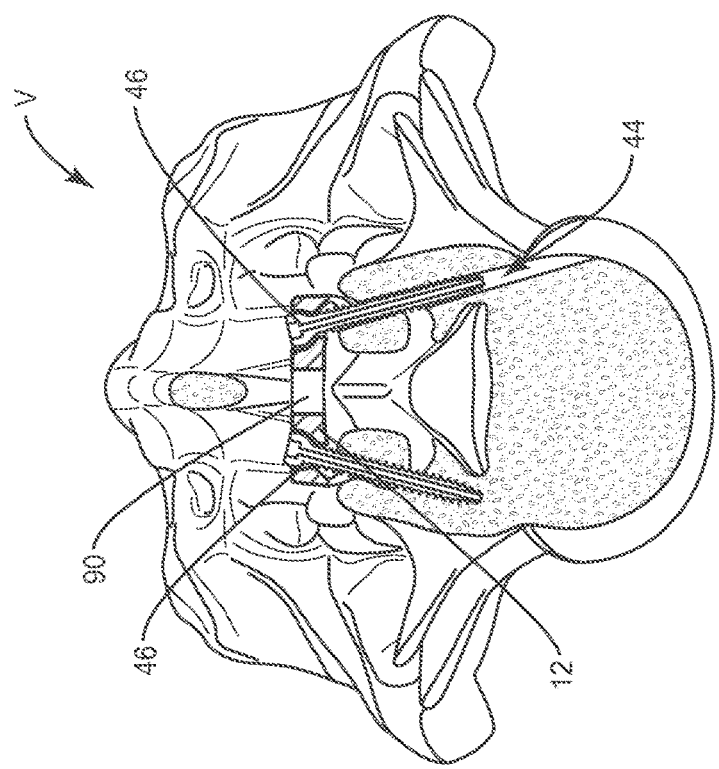
FIG. 9 is an axial view of components of one embodiment of a surgical system in accordance with the principles of the present disclosure disposed with vertebrae.

End member 14 includes an inner surface 40 that defines opening 42. In some embodiments, opening 42 is oriented along a direct facet-pedicle pathway 44, as shown in FIGS. 9 and 10. In some embodiments, opening 42 is oriented along a direct posterior-anterior pathway. In some embodiments, opening 42 is oriented along a pathway aligned with a plane disposed in substantially parallel relation to a sagittal plane of vertebrae. Pathway 44 is configured for disposal of a fastener 46, as described herein. In some embodiments, pathway 44 is disposed at an angular range a relative to axis X1, as shown in FIGS. 8 and 10. In some embodiments, angular range a includes an angle in a range of 0 to 40 degrees relative to axis X1.

Plate 12 includes an end member 50, which includes an anterior surface 52 and a posterior surface 54. Surface 52 is configured to engage tissue, such as, for example, vertebrae, as described herein. End member 50 includes a surface, such as, for example, an end surface 56. In some embodiments, surface 56 includes an undulating profile. In some embodiments, surface 56 may have alternate configurations, such as, for example, arcuate, irregular, uniform, non-uniform, variable and/or tapered. Surface 56 extends between surfaces 52, 54.

End member 50 includes a tissue engaging surface 58 engageable with vertebrae. In some embodiments, surface 58 includes an undulating profile. In some embodiments, surface 58 may have alternate configurations, such as, for example, arcuate, irregular, uniform, non-uniform, variable and/or tapered. Surface 58 extends between surfaces 52, 54. End member 50 includes a surface 60 configured for engagement with tissue, such as, for example, a spinous process. In some embodiments, surface 60 includes an angled profile. In some embodiments, surface 60 may have alternate configurations, such as, for example, arcuate, irregular, uniform, non-uniform, variable and/or tapered. Surface 60 extends between surfaces 52, 54. In some embodiments, surfaces 58, 60 may be rough, textured, porous, semi-porous, dimpled, knurled, toothed, grooved and/or polished to facilitate engagement with tissue.

End member 50 includes a surface 66 that defines a slot 68 having an arcuate configuration. Slot 68 defines a portion of track 34. Slot 68 is configured for disposal of an intermediate member 90, as described herein, and surface 66 is engageable with intermediate member 90 in a keyed connection. Slot 68 includes a retention member, such as, for example, opposing flanges 70 disposed along slot 68 and configured to engage a portion of intermediate member 90 to retain intermediate member 90 with end member 50. As intermediate member 90 translates relative to end member 50, flanges 70 retain intermediate member 90 with end member 50.

End member 50 includes an inner surface 72 that defines opening 74. In some embodiments, opening 74 is oriented along a direct facet-pedicle pathway 76, as shown in FIGS. 9 and 10. In some embodiments, opening 74 is oriented along a direct posterior-anterior pathway. In some embodiments, opening 74 is oriented along a pathway aligned with a plane disposed in substantially parallel relation to a sagittal plane of vertebrae. In some embodiments, pathway 76 is disposed at an angular range a relative to axis X1, similar to pathway 44.

Figure 4:
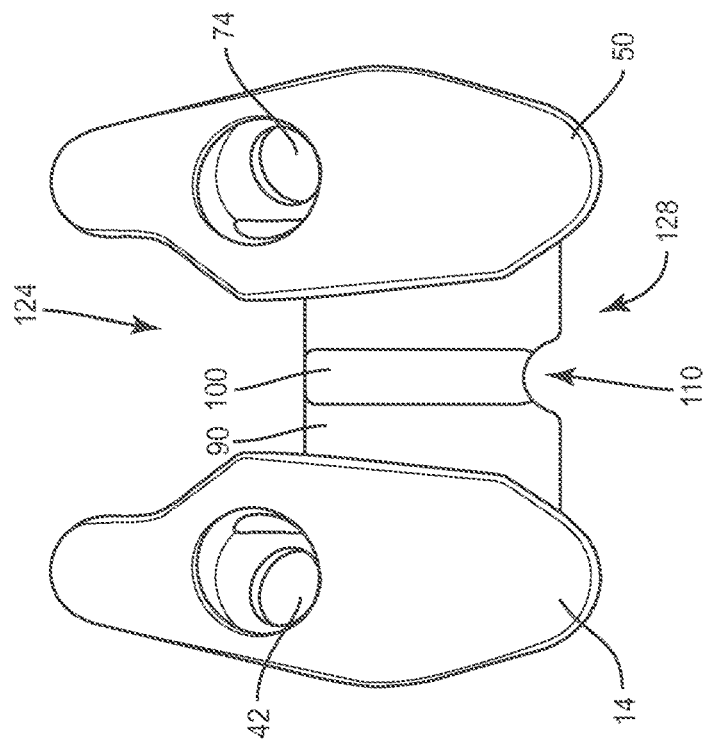
FIG. 4 is a plan view of the components shown in FIG. 1.
Figure 5:
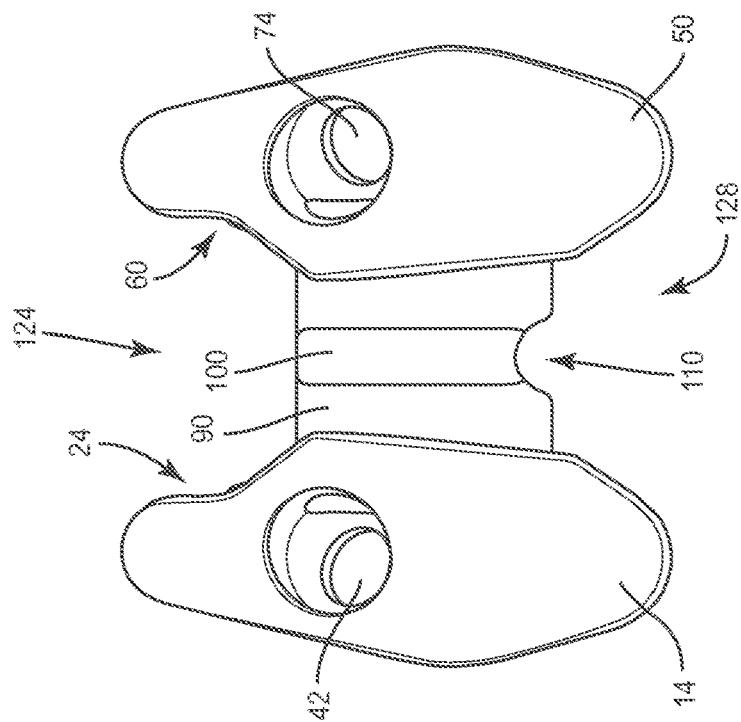
FIG. 5 is a plan view of the components shown in FIG. 1.
Figure 6:
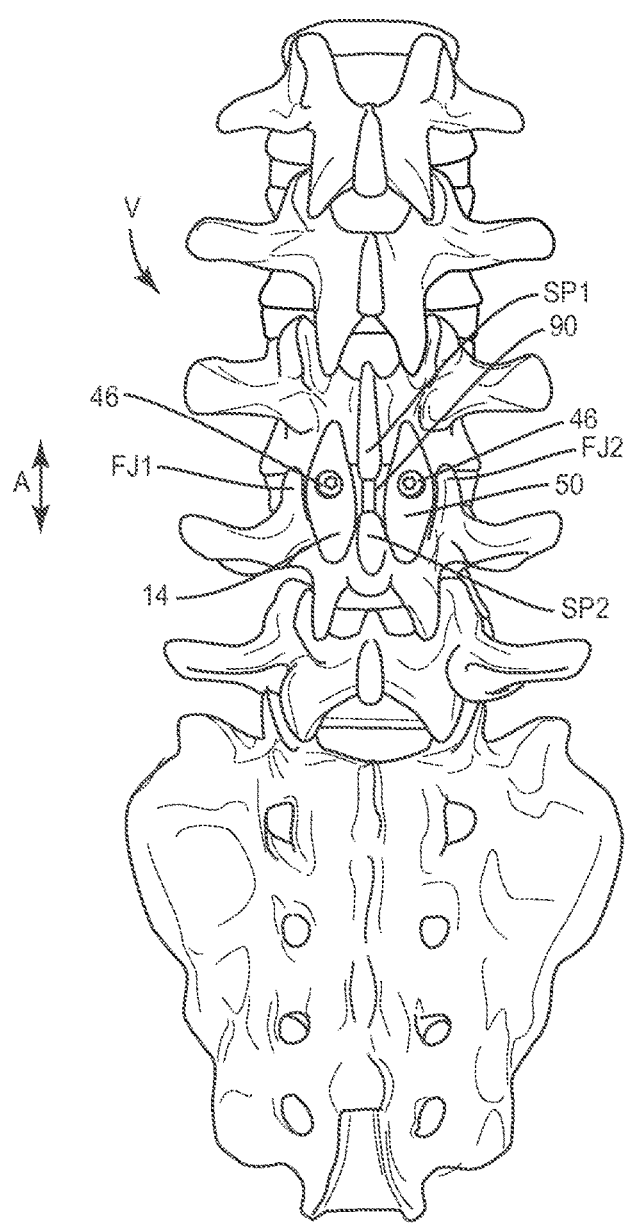
FIG. 6 is a plan view of components of one embodiment of a surgical system in accordance with the principles of the present disclosure disposed with vertebrae.
Figure 7:
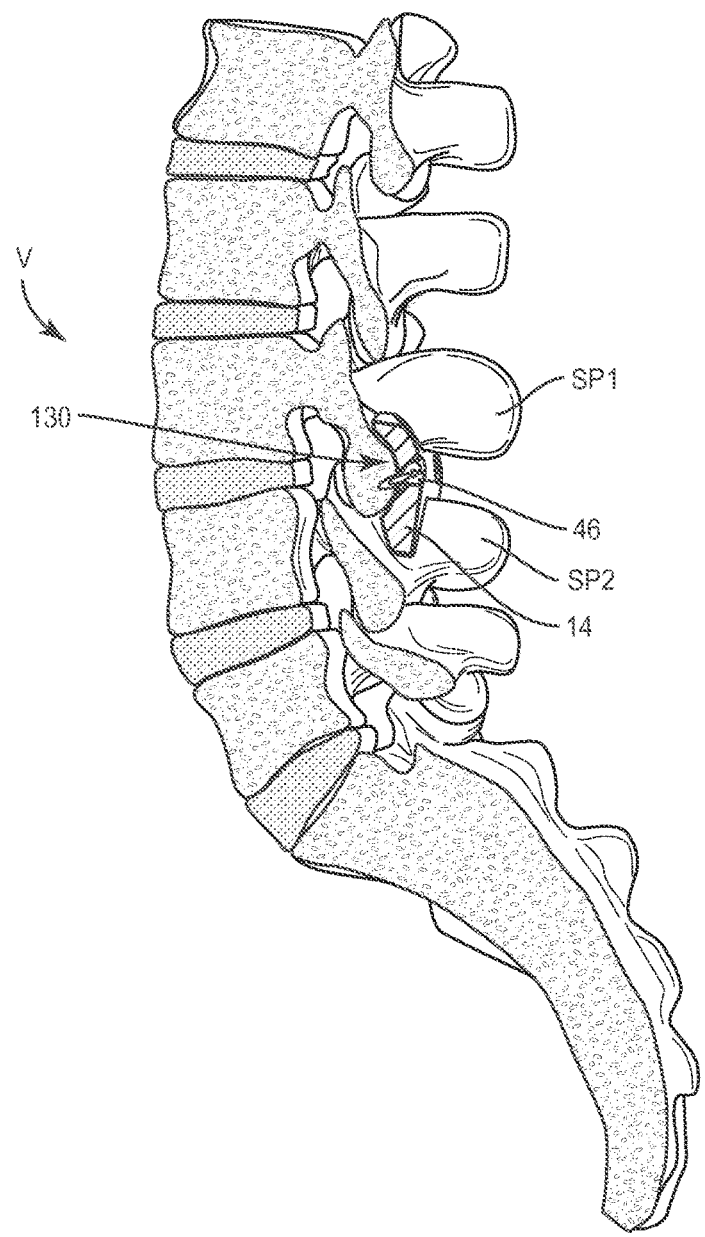
FIG. 7 is a side view of the components and vertebrae shown in FIG. 6.

Intermediate member 90 is configured for movable disposal within slots 32, 68 along track 34 for selective adjustability of plate 12 with a patient anatomy and/or positioning for attachment and/or implantation with tissue. Track 34 facilitates translation of intermediate member 90 relative to end members 14, 50 along a cranial-caudal trajectory, as shown by arrows A in FIG. 2, for selective adjustment to engage vertebrae and/or orient an openings 42, 74, as described herein. In some embodiments, intermediate member 90 is translatable relative to end members 14, 50 to facilitate engagement with vertebrae, as described herein. In some embodiments, intermediate member 90 is translatable along track 34 in a range of slidable movement relative to end members 14, 50 between a superior vertebral limit, as shown in FIG. 4, and an inferior vertebral limit, as shown in FIG. 5.

In some embodiments, intermediate member 90 is translatable along track 34 relative to openings 42, 74 to facilitate engagement of fasteners 46 with vertebrae, such as, for example, facets/pedicles and accommodate variation in patient anatomies and/or different spinal levels of a patient. In some embodiments, end member 14 is movable relative to end member 50 and/or intermediate member 90. In some embodiments, end member 50 is movable relative to end member 14 and/or intermediate member 90.

Intermediate member 90 is configured to connect end member 14 with end member 50 to form a modular plate 12 to facilitate selective adjustability of plate 12 relative to adjacent vertebrae. In some embodiments, surgical system 10 comprises a kit including a plurality of alternate intermediate members 90 having varying width and/or height to facilitate engagement with varied patient anatomy. Intermediate member 90 includes an anterior surface 92 and a posterior surface 94. Intermediate member 90 extends between an end 96 and an end 98.

Surface 94 includes a protrusion 100. Protrusion 100 extends between an end 102 and an end 104. Protrusion 100 extends a distance from surface 94 and is configured for disposal between vertebrae, such as, for example, spinous process'. In some embodiments protrusion 100 comprises a handle to facilitate translation of intermediate member 90 and/or positioning of plate 12.

End 102 includes a surface 106 engageable with vertebrae, such as, for example, a spinous process and/or a lamina/spinous process intersection. End 104 includes a surface 108 engageable with vertebrae, such as, for example, a spinous process and/or a lamina/spinous process intersection. End 104 includes an arcuate portion 110 engageable with vertebrae and contoured to a shape of a spinous process.

Intermediate member 90 includes an edge, such as, for example, a keyed portion 112 disposable with slot 32 during translation of intermediate member 90 relative to member 14. Portion 112 includes an enlarged portion 114 that extends between ends 96, 98. Portion 114 is disposed with slot 32 and engageable with opposing flanges 36 in a movably locked orientation with member 14 to retain and prevent removal of intermediate member 90 from slot 32 during relative translation. Intermediate member 90 includes an edge, such as, for example, a keyed portion 120 disposable with slot 68 during translation of intermediate member 90 relative to member 50. Portion 120 includes an enlarged portion 122 that extends between ends 96, 98. Portion 122 is disposed with slot 68 and engageable with opposing flanges 70 in a movably locked orientation with member 50 to retain and prevent removal of intermediate member 90 from slot 68 during relative translation.

Surfaces 22, 106, 58 define a cavity 124. Cavity 124 is configured for disposal of vertebrae, such as, for example, a spinous process and/or a lamina/spinous process intersection. In some embodiments, cavity 124 is arcuate in shape. In some embodiments, cavity 124 may have alternate configurations, such as, for example, irregular, uniform, non-uniform, variable and/or tapered. In some embodiments, the configuration and dimension of cavity 124 is adjustable via translation of intermediate member 90 relative to end members 14, 50.

Surfaces 24, 108, 60 define a cavity 128. Cavity 128 is configured for disposal of vertebrae, such as, for example, a spinous process and/or a lamina/spinous process intersection. In some embodiments, cavity 128 includes a trapezoid profile. In some embodiments, cavity 128 may have alternate configurations, such as, for example, angled, arcuate, irregular, uniform, non-uniform, variable and/or tapered. In some embodiments, the configuration and dimension of cavity 128 is adjustable via translation of intermediate member 90 relative to end members 14, 50.

Figure 3:
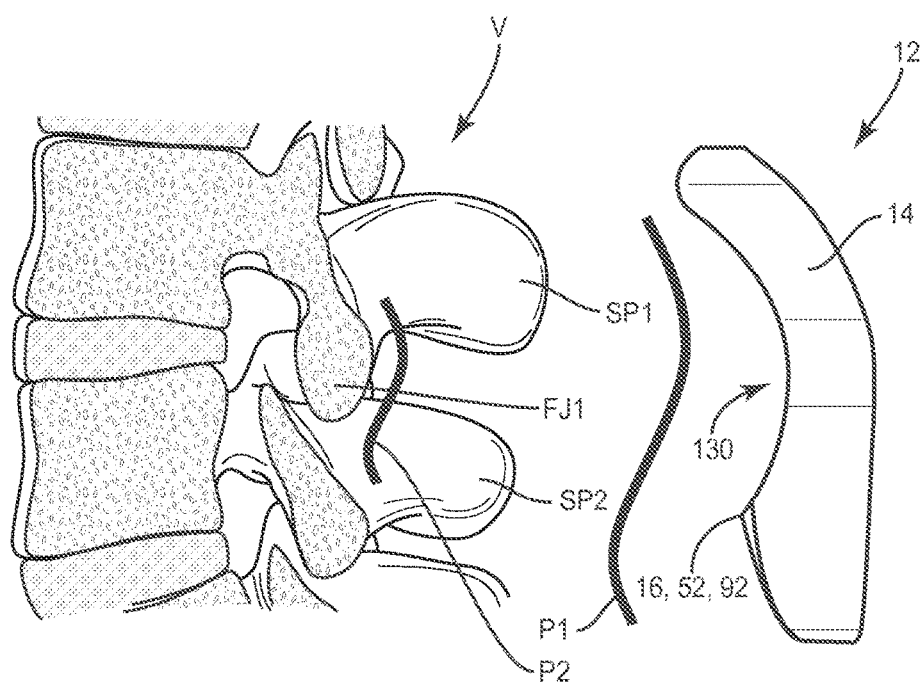
FIG. 3 is a side view of the components shown in FIG. 1 and vertebrae.

Surfaces 16, 52, 92 define a tissue mating curvature 130 of plate 12, as shown in FIG. 3. Curvature 130 includes a profile P1 that matches and/or mates with a profile P2 of vertebrae V. As such, curvature 130 is configured for selective engagement with vertebrae, such as, for example, a spinous process, lamina, tissue adjacent a lamina/spinous and/or tissue adjacent facet joints. In some embodiments, curvature 130 includes an undulating profile. In some embodiments, curvature 130 is adjustable via translation of intermediate member 90 relative to end members 14, 50.

For example, curvature 130 is contoured and engages flush with tissue to mate profile P1 with profile P2 of vertebrae V such that plate 12 conforms with the anatomy of adjacent facet joints FJ1, FJ2 and/or other adjacent tissue. Curvature 130 facilitates stability between plate 12 and vertebrae. In some embodiments, curvature 130 may have alternate configurations, such as, for example, arcuate, irregular, uniform, non-uniform, variable and/or tapered. In some embodiments, profile P1 mates with profile P2 to provide stability and an effective screw trajectory.

In assembly, operation and use, surgical system 10, similar to the systems and methods described herein, is employed to treat a selected section of vertebrae V, as shown in FIGS. 6-10. A medical practitioner obtains access to a surgical site including vertebrae V in any appropriate manner, such as through incision and retraction of tissues. In some embodiments, surgical system 10 can be used in any existing surgical method or technique including open surgery, mini-open surgery, minimally invasive surgery and percutaneous surgical implantation, whereby vertebrae V is accessed through a mini-incision, or sleeve that provides a protected passageway to the area. Once access to the surgical site is obtained, the particular surgical procedure can be performed for treating a spine disorder. In some embodiments, one or all of the components of surgical system 10 can be delivered or implanted as a pre-assembled device or can be assembled in situ. The components of surgical system 10 may be completely or partially revised, removed or replaced.

An incision is made in the body of a patient and a cutting instrument (not shown) creates a surgical pathway for implantation of components of surgical system 10 with a portion of vertebrae V including spinous process SP1, spinous process SP2, facet joint FJ1 and facet joint FJ2. A preparation instrument (not shown) can be employed to prepare tissue surfaces of vertebrae V, as well as for aspiration and irrigation of a surgical region.

Pilot holes are made in vertebrae V1, V2 for receiving fixation elements, such as, for example, fasteners 46. Pilot holes are oriented along facet-pedicle pathways 44, 76, as described herein. Plate 12, as described herein, is delivered and introduced to the surgical site adjacent spinous process SP1, spinous process SP2, facet joint FJ1 and facet joint FJ2. Spinous process SP1 is disposed with cavity 124 and spinous process SP2 is disposed with cavity 128.

Intermediate member 90 and end members 14, 50 are slidably and selectively adjusted, as described herein, such that plate 12 conforms to the anatomy of spinous process SP1, spinous process SP2, facet joint FJ1 and facet joint FJ2. Intermediate member 90 is translated relative to end members 14, 50 along track 34 and a cranial-caudal trajectory, as shown by arrows A in FIG. 6.

Surface 106 engages spinous process SP1 and surface 108 engages spinous process SP2. This configuration provides for selective adjustment of plate 12 to engage vertebrae and orient openings 42, 74, as described herein. Intermediate member 90 and end members 14, 50 are slidably and selectively adjusted to align openings 42, 74 with the pilot holes to accommodate variation in anatomy at different vertebral levels. Fasteners 46 are disposed with openings 42, 74 and engaged with vertebrae V to fasten plate 12 with vertebrae V1, V2.

Upon selective orientation of plate 12 with the anatomy of spinous process SP1, spinous process SP2, facet joint FJ1 and facet joint FJ2, curvature 130 engages flush with tissue to mate profile P1 with profile P2, as described herein. Plate 12 conforms with the anatomy of spinous process SP1, spinous process SP2, facet joint FJ1 and facet joint FJ2, and/or adjacent tissue.

Figure 11:
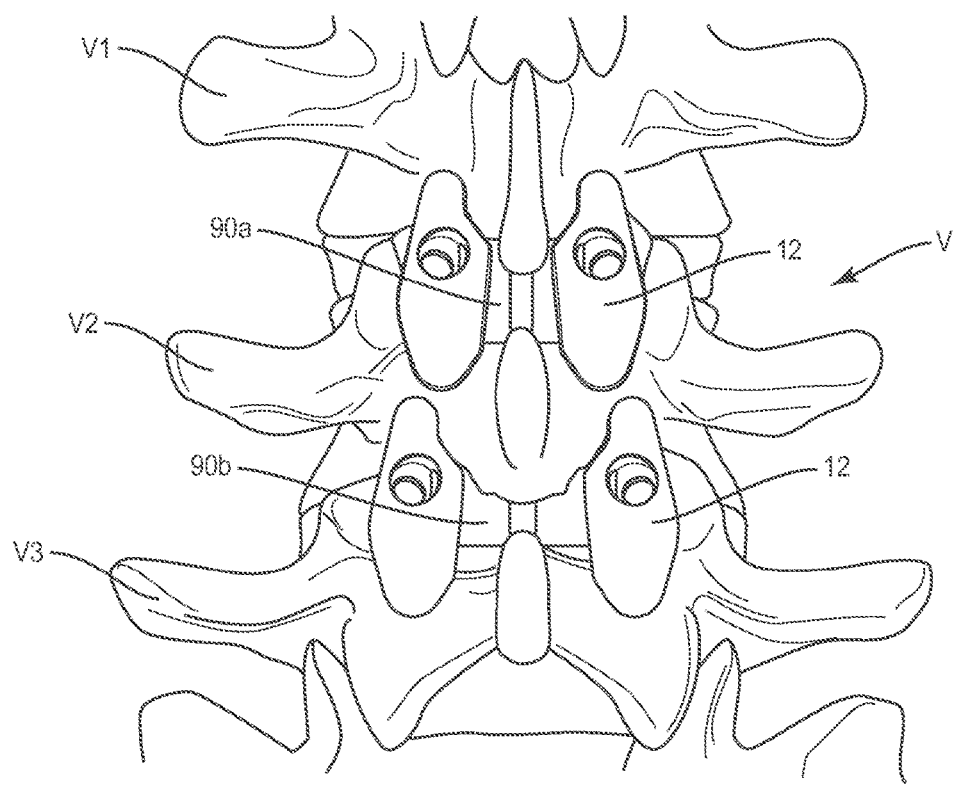
FIG. 11 is a plan view of components of one embodiment of a surgical system in accordance with the principles of the present disclosure disposed with vertebrae.
Figure 12:
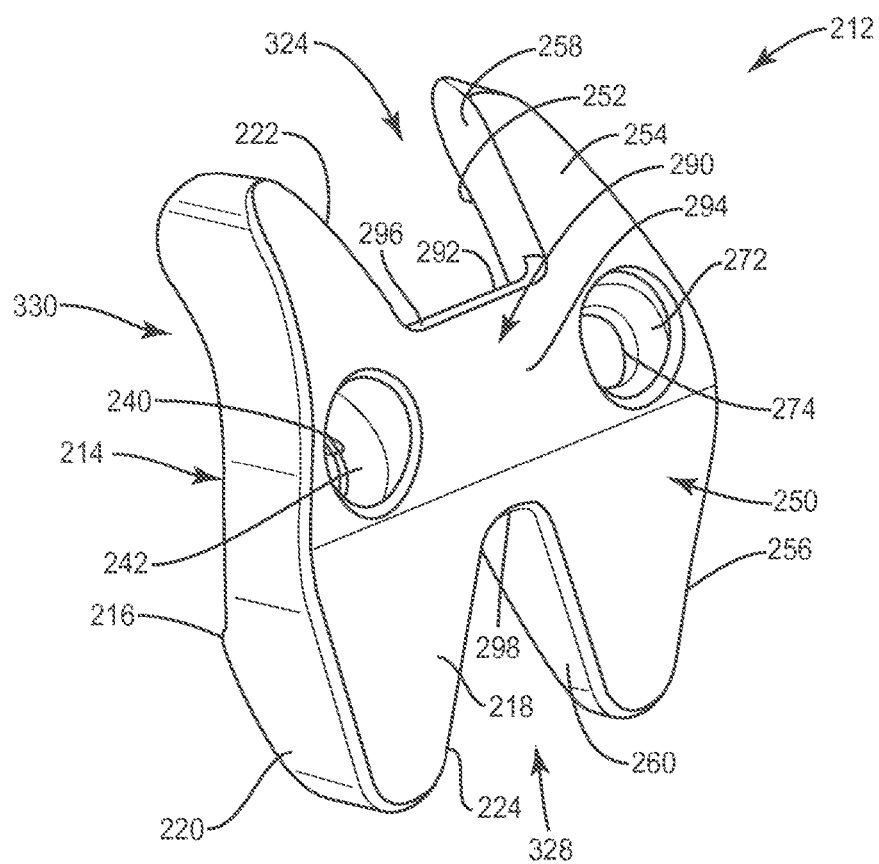
FIG. 12 is a perspective view of components of one embodiment of a surgical system in accordance with the principles of the present disclosure.
Figure 15:
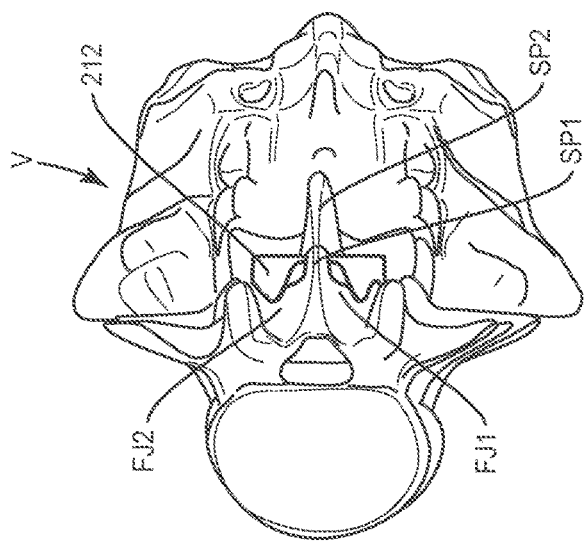
FIG. 15 is an axial view of the components and vertebrae shown in FIG. 13.
Figure 14:
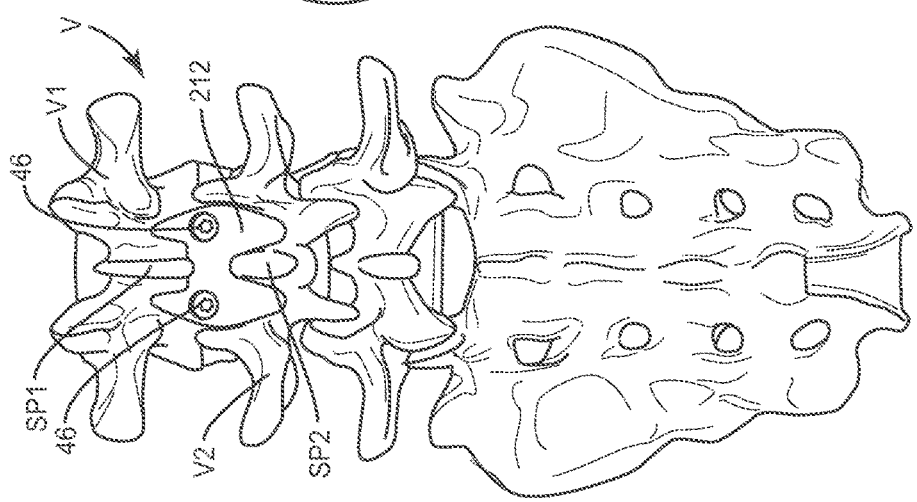
FIG. 14 is a plan view of the components and vertebrae shown in FIG. 13.

In one embodiment, as shown in FIG. 11, spinal implant system 10 comprises a kit including a plurality of alternate interspinous implants comprising a plurality of modular plates 12, similar to that described herein. The modular plates 12 can be of alternate configuration and dimension and include end members 14, 50 described herein, and one of a plurality of alternately configured and dimensioned intermediate members 90a, 90b, similar to intermediate member 90 described herein. A superior oriented plate 12 includes intermediate member 90a having a smaller width to conform with the anatomy of vertebrae V1, V2, similar to that described herein. An inferior oriented plate 12 includes intermediate member 90b having a larger width to conform with the anatomy of vertebrae V2, V3, similar to that described herein.

In some embodiments, spinal implant system 10 can include one or a plurality of fasteners such as those described herein and/or fixation elements, which may be employed with a single vertebral level or a plurality of vertebral levels. In some embodiments, fasteners 46 may be engaged with vertebrae in various orientations, such as, for example, series, parallel, offset, staggered and/or alternate vertebral levels. In some embodiments, fasteners 46 may be configured as multi-axial screws, sagittal angulation screws, pedicle screws, mono-axial screws, uni-planar screws, fixed screws, anchors, tissue penetrating screws, conventional screws, expanding screws. In some embodiments, fasteners 46 may be employed with wedges, anchors, buttons, clips, snaps, friction fittings, compressive fittings, expanding rivets, staples, nails, adhesives, posts, connectors, fixation plates and/or posts.

In one embodiment, spinal implant system 10 includes an agent, which may be disposed, packed, coated or layered within, on, adjacent or about the components and/or surfaces of spinal implant system 10, and/or disposed with tissue. In some embodiments, the agent may include bone growth promoting material, such as, for example, bone graft to enhance fixation of the components and/or surfaces of spinal implant system 10 with vertebrae. In some embodiments, the agent may include one or a plurality of therapeutic agents and/or pharmacological agents for release, including sustained release, to treat, for example, pain, inflammation and degeneration.

Upon completion of a procedure, as described herein, the surgical instruments, assemblies and non-implanted components of spinal implant system 10 are removed and the incision(s) are closed. One or more of the components of spinal implant system 10 can be made of radiolucent materials such as polymers. Radiopaque markers may be included for identification under x-ray, fluoroscopy, CT or other imaging techniques. In some embodiments, the use of surgical navigation, microsurgical and image guided technologies may be employed to access, view and repair spinal deterioration or damage, with the aid of spinal implant system 10.

In one embodiment, as shown in FIGS. 12-15, spinal implant system 10, similar to the systems and methods described herein, includes a plate 212, similar to plate 12 described herein. Plate 212 defines a longitudinal axis X2. Plate 212 includes an end member 214, which includes an anterior surface 216 and a posterior surface 218. Surface 216 is configured to engage spinous process SP1, spinous process SP2, facet joint FJ1, facet joint FJ2 and/or adjacent tissue, similar to surface 16 described herein. End member 214 includes an end surface 220 that extends between surfaces 216, 218.

End member 214 includes a tissue engaging surface 222 engageable with spinous process SP1 and extending between surfaces 216, 218. End member 214 includes a surface 224 configured for engagement with spinous process SP2. Surface 224 extends between surface 216, 218. In some embodiments, surfaces 222, 224 may be rough, textured, porous, semi-porous, dimpled, knurled, toothed, grooved and/or polished to facilitate engagement with tissue.

End member 214 includes an inner surface 240 that defines an opening 242, similar to opening 42 described herein, which is oriented along a pathway, similar to pathway 44 described herein.

Plate 212 includes an end member 250, which includes an anterior surface 252 and a posterior surface 254. Surface 252 is configured to engage spinous process SP1, spinous process SP2, facet joint FJ1, facet joint FJ2 and/or adjacent tissue, similar to surface 52 described herein. End member 250 includes an end surface 256 that extends between surfaces 252, 254.

End member 250 includes a tissue engaging surface 258 engageable with spinous process SP1 and extending between surfaces 252, 254. End member 250 includes a surface 260 configured for engagement with spinous process SP2 and extending between surfaces 252, 254. In some embodiments, surfaces 258, 260 may be rough, textured, porous, semi-porous, dimpled, knurled, toothed, grooved and/or polished to facilitate engagement with tissue.

End member 250 includes an inner surface 272 that defines opening 274, similar to opening 74 described herein, which is oriented along a pathway, similar to pathway 76 described herein.

An intermediate member 290 connects and is monolithically formed with end members 214, 250. Intermediate member 290 includes an anterior surface 292 and a posterior surface 294. Intermediate member 290 extends between an end 296 and an end 298. Surfaces 222, 296, 258 define a cavity 324. Cavity 324 is configured for disposal of spinous process SP1. Surfaces 224, 298, 260 define a cavity 328. Cavity 328 is configured for disposal of spinous process SP2.

Figure 13:
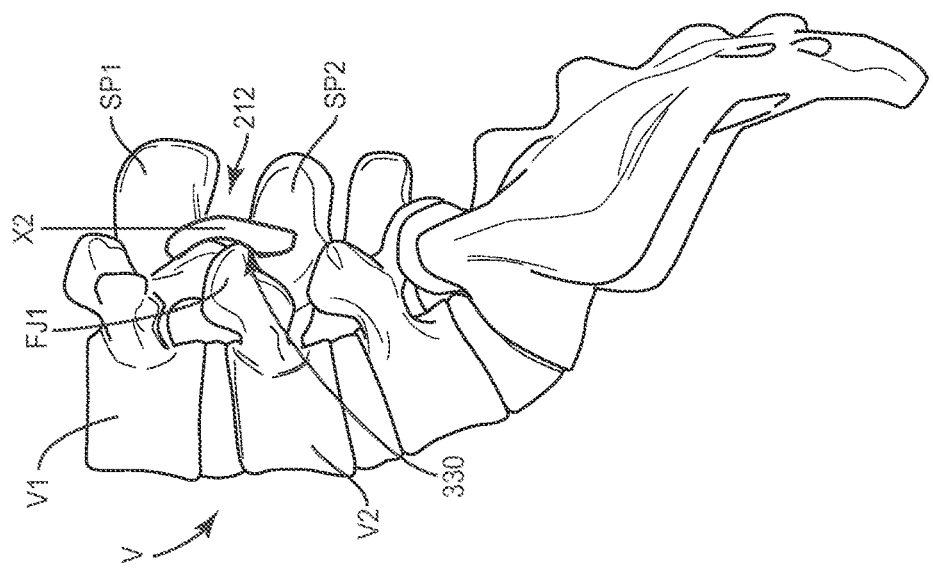
FIG. 13 is a side view of components of one embodiment of a surgical system in accordance with the principles of the present disclosure disposed with vertebrae.

Surfaces 216, 252, 292 define a tissue mating curvature 330, similar to curvature 130 described herein. Curvature 330 includes a profile that matches and/or mates with a profile of vertebrae V, as shown in FIG. 13. For example, curvature 330 is contoured and engages flush with tissue to mate with vertebrae V such that plate 212 conforms with the anatomy of adjacent facet joints FJ1, FJ2 and/or other adjacent tissue. Curvature 330 facilitates stability between plate 212 and vertebrae. In some embodiments, curvature 330 includes an inferior portion and/or a foot configured to provide stability when disposed with an inferior lamina.

Figure 16:
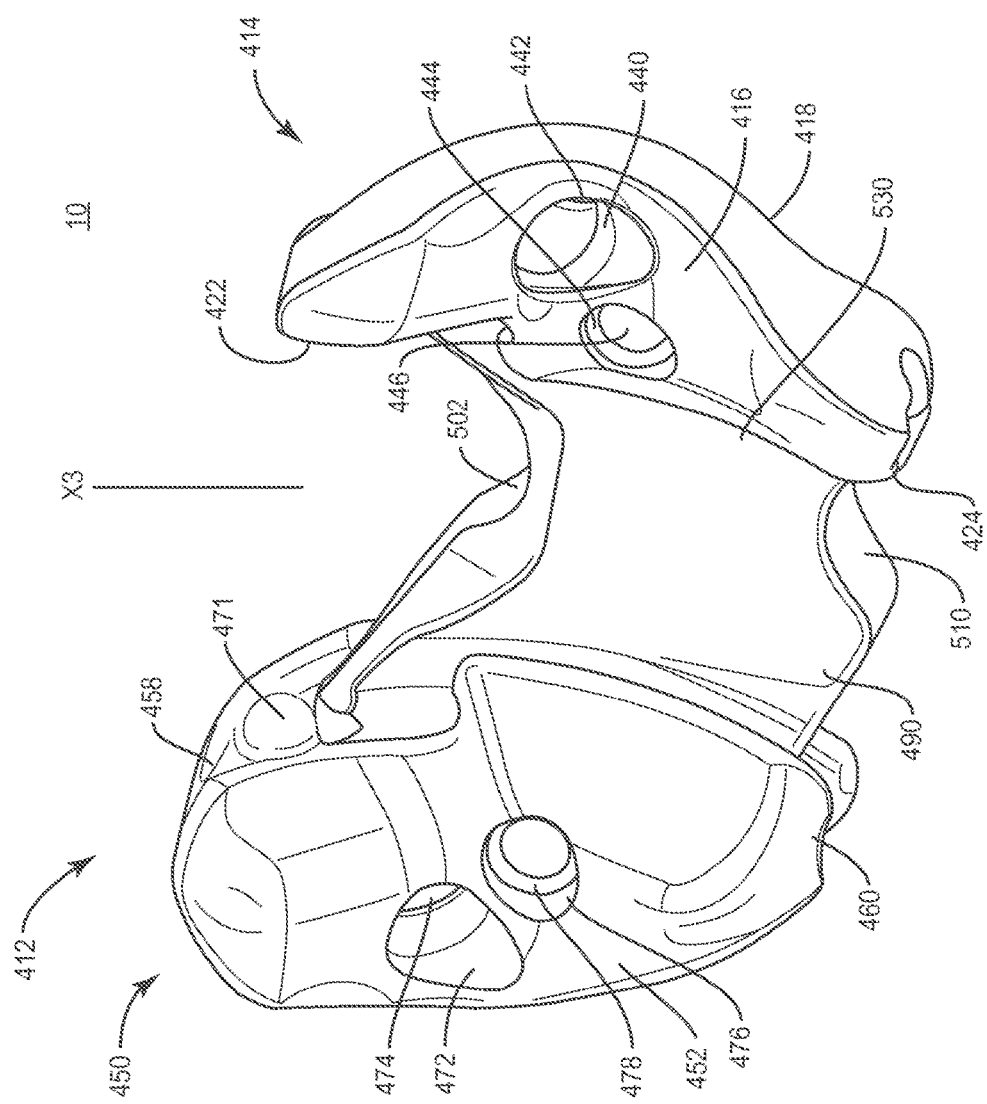
FIG. 16 is a perspective view of components of one embodiment of a surgical system in accordance with the principles of the present disclosure.
Figure 17:
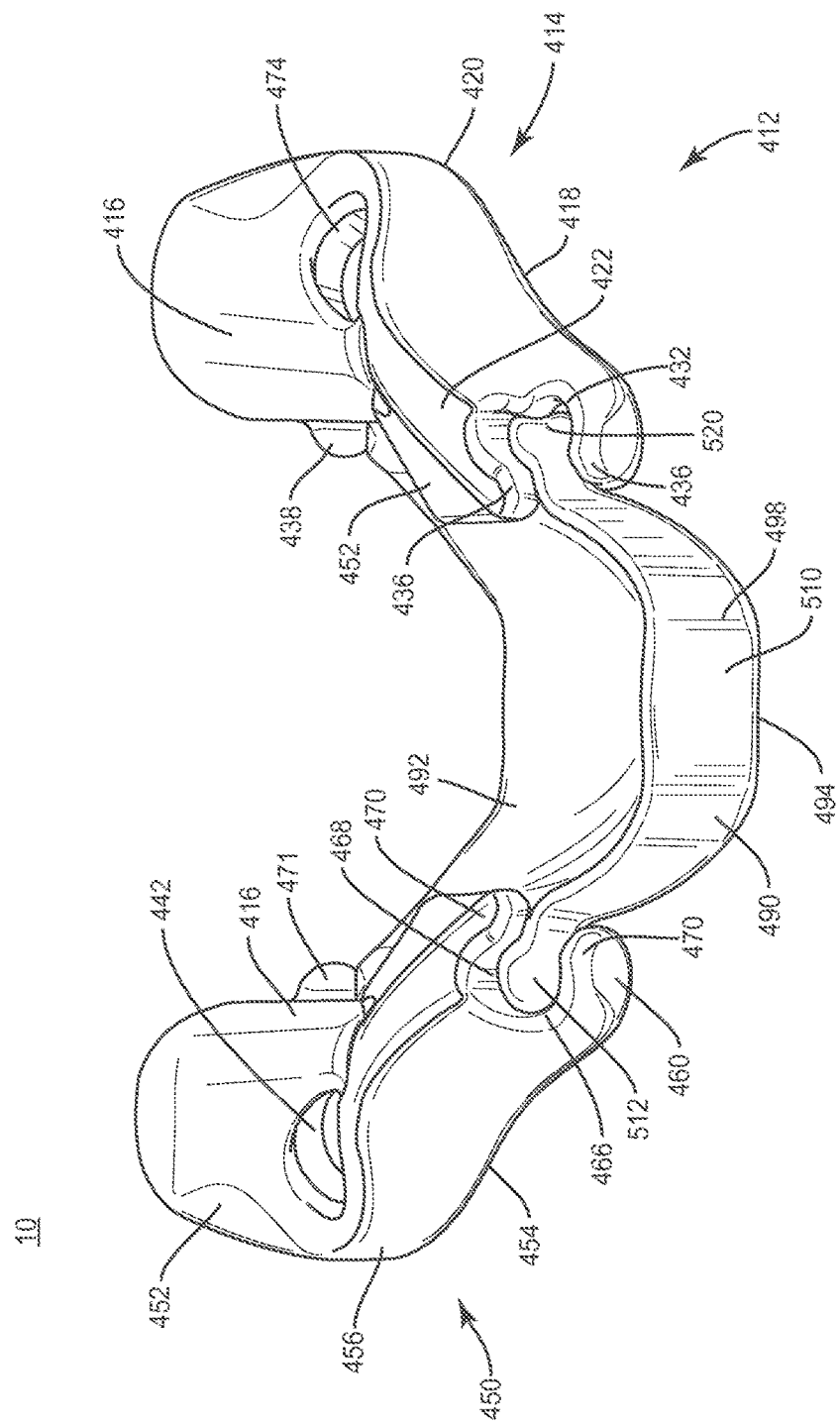
FIG. 17 is a side view of the components shown in FIG. 16.
Figure 18:
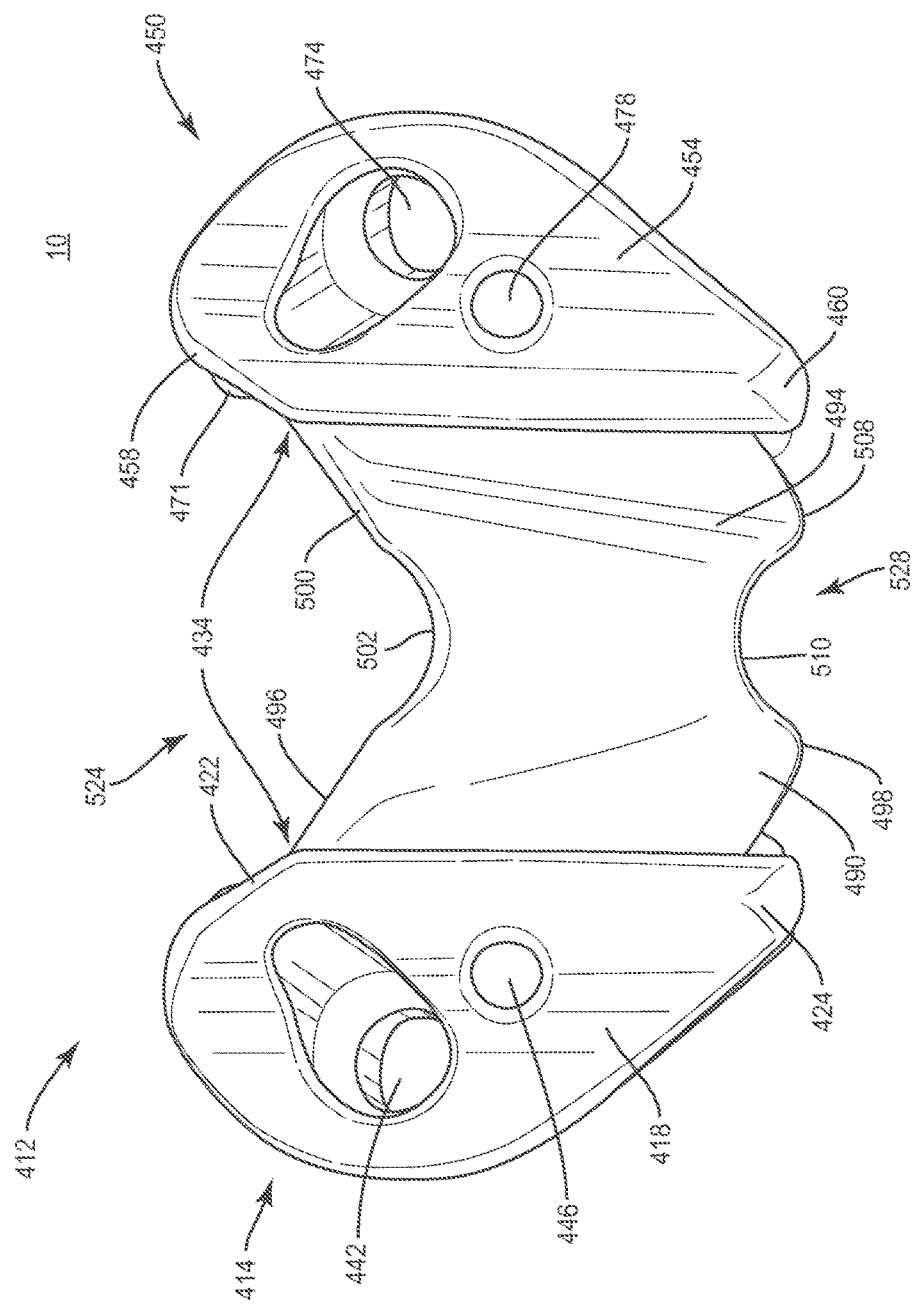
FIG. 18 is a side view of the components shown in FIG. 16.

In one embodiment, as shown in FIGS. 16-18, spinal implant system 10, similar to the systems and methods described herein, includes a plate 412, similar to plate 12 described herein. In some embodiments, plate 412 is modular and comprises end members, as described herein, to facilitate selective adjustability with a patient anatomy. Plate 412 defines a longitudinal axis X3.

Plate 412 includes an end member 414, which includes an anterior surface 416 and a posterior surface 418. Surface 416 is configured to engage tissue, such as, for example, vertebrae, as described herein. End member 414 includes an end surface 420. In some embodiments, surface 420 includes an undulating profile.

End member 414 includes a tissue engaging surface 422 engageable with vertebrae. End member 414 includes a surface 424 configured for engagement with tissue, such as, for example, a spinous process. In some embodiments, surface 422 and/or surface 424 can be disposed for clearance with an inferior lamina.

End member 414 includes a surface 430 that defines a slot 432. Slot 432 defines a portion of a pathway, such as, for example, a track 434, similar to track 34, as described herein. Slot 432 is configured for disposal of an intermediate member 490, as described herein. Surface 430 includes opposing flanges 436 disposed along slot 432 and configured to engage a portion of intermediate member 490 to retain intermediate member 490 with end member 414. Surface 430 includes a protrusion, such as, for example, a bump stop 438. In some embodiments, bump stop 438 resists and/or prevents intermediate member 490 from sliding entirely out of track 434. In some embodiments, the protrusion may have various configurations, such as, for example, oval, oblong, triangular, rectangular, square, polygonal, irregular, uniform, non-uniform, variable and/or tapered.

End member 414 includes an inner surface 440 that defines an opening 442, similar to opening 42 described herein, configured for disposal of a fastener, as described herein. End member 414 includes an inner surface 444 that defines a central opening 446 configured for engagement with a surgical instrument, such as, for example, an insertion tool to facilitate insertion of plate 412 with a surgical site.

Plate 412 includes an end member 450, which includes an anterior surface 452 and a posterior surface 454. Surface 452 is configured to engage tissue, such as, for example, vertebrae, as described herein. End member 450 includes an end surface 456. In some embodiments, surface 456 includes an undulating profile.

End member 450 includes a tissue engaging surface 458 engageable with vertebrae. End member 450 includes a surface 460 configured for engagement with tissue, such as, for example, a spinous process. In some embodiments, surface 458 and/or surface 460 can be disposed for clearance with an inferior lamina.

End member 450 includes a surface 466 that defines a slot 468. Slot 468 defines a portion of track 434. Slot 468 is configured for disposal of intermediate member 490, as described herein. Slot 468 includes opposing flanges 470 disposed along slot 468 and configured to engage a portion of intermediate member 490 to retain intermediate member 490 with end member 450. Surface 466 includes a protrusion, such as, for example, a bump stop 471, similar to stop 438. In some embodiments, bump stop 471 resists and/or prevents intermediate member 490 from sliding entirely out of track 434.

End member 450 includes an inner surface 472 that defines opening 474, similar to opening 74 described herein, configured for disposal of a fastener, as described herein. End member 450 includes an inner surface 476 that defines a central opening 478 configured for engagement with a surgical instrument, such as, for example, an insertion tool to facilitate insertion of plate 412 into a surgical site.

Intermediate member 490 is configured for movable disposal within slots 432, 468 along track 434 for selective adjustability of plate 412 with a patient anatomy and/or positioning for attachment and/or implantation with tissue, as described herein. Track 434 facilitates translation of intermediate member 490 relative to end members 414, 450 along a cranial-caudal trajectory, as described herein, for selective adjustment to engage vertebrae and/or orient openings 442, 474, similar to that described herein. In some embodiments, intermediate member 490 is translatable relative to end members 414, 450 to facilitate engagement with vertebrae, as described herein. In some embodiments, intermediate member 490 is translatable along track 434 in a range of slidable movement relative to end members 414, 450 between a superior vertebral limit and an inferior vertebral limit, as described herein.

Intermediate member 490 is configured to connect end member 414 with end member 450 to form a modular plate 412 to facilitate selective adjustability of plate 412 relative to adjacent vertebrae, similar to that described herein. Intermediate member 490 includes an anterior surface 492 and a posterior surface 494. Intermediate member 490 extends between an end 496 and an end 498. In some embodiments, intermediate member 490 mates with an inferior spinous process more posterior than the superior spinous process such that an inferior surface of plate 412 does not project inside the spinal canal.

End 496 includes a surface 500 engageable with vertebrae, such as, for example, a spinous process and/or a lamina/spinous process intersection. End 496 includes a portion 502 engageable with vertebrae and contoured to a shape of a spinous process. End 498 includes a surface 508 engageable with vertebrae, such as, for example, a spinous process and/or a lamina/spinous process intersection. End 498 includes a portion 510 engageable with vertebrae and contoured to a shape of a spinous process. In some embodiments, portion 502 comprises a notch on a superior surface of intermediate member 490 and portion 510 comprises an inferior notch that provide for stabilization and centering of plate 412 with spinous processes.

Intermediate member 490 includes an edge, such as, for example, a keyed portion 512, similar to portion 112, disposable with slot 432 during translation of intermediate member 490 relative to member 414. Intermediate member 490 includes an edge, such as, for example, a keyed portion 520, similar to portion 120, disposable with slot 468 during translation of intermediate member 490 relative to member 450.

Surfaces 422, 500, 458 define a cavity 524, similar to cavity 124, configured for disposal of vertebrae, such as, for example, a spinous process and/or a lamina/spinous process intersection. Surfaces 424, 508, 460 define a cavity 528. Cavity 528 is configured for disposal of vertebrae, such as, for example, a spinous process and/or a lamina/spinous process intersection. Surfaces 416, 452, 492 define a tissue mating curvature 530, similar to cavity 130, of plate 412, as shown in FIG. 17. Curvature 530 includes a profile that matches and/or mates with a profile of vertebrae, as described herein.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. An interspinous implant comprising:
    a first member extending along a longitudinal axis between opposite first and second ends, the first member comprising an inner surface defining a slot extending from the first end to the second end;
    a second member extending between opposite first and second ends, the second member comprising an inner surface defining a slot extending from the first end of the second member to the second end of the second member, at least one of the members comprising an opening that extends transverse to the longitudinal axis; and
    a third member positioned within the slots and movable relative to the first member and the second member along the longitudinal axis,
    wherein a top surface of the third member and the inner surfaces define a first cavity configured for disposal of a first spinous process and a bottom surface of the third member and the inner surfaces define a second cavity configured for disposal of a second spinous process.

2. An interspinous implant as recited in claim 1, wherein the members comprise a plate including a vertebral engaging surface that defines a tissue mating curvature.

3. An interspinous implant as recited in claim 2, wherein the curvature includes an undulating profile.

4. An interspinous implant as recited in claim 1, wherein the members comprise a plate including an anterior surface and a posterior surface, the anterior surface defining a tissue mating curvature engageable with tissue of a facet joint.

5. An interspinous implant as recited in claim 1, further comprising a trans-facet joint fastener configured for disposal with the opening.

6. An interspinous implant as recited in claim 1, wherein the members are relatively movable and selectively adjustable to engage vertebrae.

7. An interspinous implant as recited in claim 1, wherein the first member and the second member are separate and connected via the third member.

8. An interspinous implant as recited in claim 1, wherein the third member is movable along the longitudinal axis in a cranial-caudal orientation.

9. An interspinous implant as recited in claim 1, wherein the third member includes a first key movable in the slot of the first member and a second key movable in the slot of the second member.

10. An interspinous implant as recited in claim 1, wherein the opening is oriented along a trans-facet fastener pathway.

11. An interspinous implant as recited in claim 1, wherein the slots are arcuate, the third member including enlarged edge portions locked with and movable in the slots.

12. An interspinous implant as recited in claim 1, wherein the opening is oriented along a direct posterior-anterior fastener pathway.

13. An interspinous implant as recited in claim 1, wherein the opening is oriented along a facet-pedicle fastener pathway.

14. An interspinous implant as recited in claim 1, wherein the bottom surface of the third member comprises an arcuate portion that defines a portion of the second cavity.

15. An interspinous implant comprising:
a first member extending between opposite first and second ends, the first member defining an opening and including an inner surface defining a slot that extends from the first end to the second end;
a second member extending between opposite first and second ends, the second member defining an opening and including an inner surface defining a slot that extends from the first end of the second member to the second end of the second member, the slots defining an arcuate track and the members including a vertebral engaging surface that defines a tissue mating curvature; and
an intermediate member movable along the track relative to the first member and the second member,
wherein a top surface of the intermediate member and the inner surfaces define a first cavity configured for disposal of a first spinous process and a bottom surface of the intermediate member and the inner surfaces define a second cavity configured for disposal of a second spinous process.

16. An interspinous implant as recited in claim 15, wherein the members are relatively movable and selectively adjustable to engage vertebrae and/or orient the openings.

17. An interspinous implant as recited in claim 15, wherein the members include a posterior surface opposite the vertebral engaging surface, the intermediate member having a protrusion that extends outwardly from the posterior surface.

18. A plate comprising:
a first member extending between opposite first and second ends, the first member including an inner surface that defines a slot that extends from the first end to the second end;
a second member extending between opposite first and second ends, the second member including an inner surface that defines a slot that extends from the first end of the second member to the second end of the second member; and
an intermediate member extending between opposite first and second ends, the intermediate member comprising side surfaces that are each movably disposed within one of the slots,
a top surface of the intermediate member and the inner surfaces defining a first cavity configured for disposal of a first spinous process and a bottom surface of the intermediate member and the inner surfaces defining a second cavity configured for disposal of a second spinous process,
the plate including a vertebral engaging surface that defines a tissue mating curvature.

19. A plate as recited in claim 18, wherein the curvature includes an undulating profile.

20. A plate as recited in claim 18, wherein the plate defines a longitudinal axis and at least one fastener opening being oriented in an angular range of 0 through 40 degrees relative to the longitudinal axis.

* * * * *